US00PP10363P

United States Patent [19]

Mak

[11] Patent Number: Plant 10,363

[45] Date of Patent: Apr. 28, 1998

[54] LILY PLANT LILIUM 'INDIA'

[76] Inventor: Johan A. Mak, 5595 Halls Ferry Rd., Independence, Oreg. 97351

[21] Appl. No.: 752,649

[22] Filed: Nov. 20, 1996

[51] Int. Cl.[6] ..... A01H 5/00

[52] U.S. Cl. ..... Plt./87.4

[58] Field of Search ..... Plt./87.4

*Primary Examiner*—James R. Feyrer

[57] ABSTRACT

A new variety of hybrid lily plant bears large clusters of flowers of excellent form and long persistence. The flowers of the new plant are particularly characterized by their consistently outward-facing flowers which are close to its stem. This combination is completely new in the Asiatic hybrid lilies. The plant is highly resistant to disease. It is an excellent pot plant as well as garden plant. The bulbs may be precooled and forced for pot flower production. The clone is vigorous and is a good grower and propagator.

1 Drawing Sheet

BACKGROUND OF THE INVENTION

My new variety of hybrid lily plant, which I call "India", originated as a seedling selected from a growing in a cultivated area at Independence, Oreg. The seedlings resulted from breeding efforts carried on by me since 1977. The breeding efforts had as their objective the production of fast growing outward-facing Asiatic lilies in red color, its flowers close to a truly genetic short stem which is suited for pot-flower production.

I achieved the desired objective by using as the seed parent a short red seedling clone produced by crossing an unnamed outward-facing red clone; the pollen parent was an orange-colored seedling selected from the same cross. The parental seedlings were selected because of their tendency to produce hybrids with outward-facing flowers and short stems.

The flowers of my new plant are characterized by a consistently outward-facing position, a red coloration, and broad-tepalled "cup-shaped" form, unusually thick substance. In addition, the clone possesses to a high degree the desirable characteristics of hybrid vigor, great hardiness, and disease resistance. It possesses all of the desired characteristics of excellence of form, color, and habit. Its flowers are produced on a single stalk. The clone is vigorous and a good grower and propagator, as observed at Independence, Oreg.

This combination is completely new in the Asiatic hybrid divisions of lilies suited for forcing of pot growing and to mass commercial cultivation. The variety is highly resistant to botrytus disease and shows tolerance of virus. The bulbs may be precooled and forced for pot-flower production. The clone is vigorous and is a good grower and propagator.

My new variety of lily plant has been asexually reproduced by me and under my direction at't Zand, Netherlands, and at Independence, Oreg. Successive generations produced by bulb scale propagation, by natural propagation from bulblets, and by tissue culture propagation have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, the connection of the flower to the stem, and in particular the novel and distinctive outfacing red flowers which are close to the stem.

DESCRIPTION OF THE NEW VARIETY

The following is a detailed description of my new variety of Asiatic hybrid lily, with nomenclature according to the *International Lily Register* (Royal Horticultural Society of London, Second Edition, 1969), and with color designations according to the Color Chart of The Royal Horticultural Society, published by the Society in 1966.

THE PLANT

Origin: Seedling.

*Seed parent.*—Selected red seedling.

*Pollen parent.*—Selected orange-colored seedling.

Commercial classification: Hybrid Lilium clone.

Horticultural classification: Division 1-B, outward-facing Asiatic hybrid lily, according to The Horticultural Classification of Lilies, Royal Horticultural Society of London.

Form: Single stem, erect and stately.

Height: 12 to 25 cm from bulbs 14 to 18 cm in circumference, provided their light levels are adequate; low light levels may cause "stretching".

Growth: Vigorous and upright.

Foliage quantity: Abundant.

Size of leaf: 12 to 14 cm long×1 to 2 cm wide; the leaves are slightly shorter and broader at the top of the stem.

Shape of leaf: Lanceolate (pointed).

Texture: Leathery and glossy.

Color: Deep green, lighter on lower side.

Bulb size: Any size, ranging to 20 cm circumference commercially.

Bulb color: White.

THE BUD

Form: Obtuse, ovoid, and long.

Size: 6 to 9 cm long and 4 to 7 cm in circumference just prior to opening.

Opening: Bud opens slowly, in response to morning light; this will take approximately one hour.

Color: Soft Red (R.H.S. C.C. Red 42 B –43 B) which shades into brown green at base; midribs are close to R.H.S. C.C. green group 143 C. Color is intensidied by cool temperatures.

Peduncle: Averages 1 cm, but in may elongate if light levels are too low or if bulbs have been improperly stored prior to forcing. Color is dark green with plum overlay.

THE FLOWER

Blooming habit: Annually in midseason; flowers once and profusely.

Size: Flowers are 10 to 15 cm in diameter, the outer tepals are 2 to 2.5 cm wide, the inner circle of tepals are 2.5–3.5 cm wide.

Borne: In a single umbel inflorescence producing 6 to 10 buds from a bulb 15 to 18 cm in circumference.

Shape: First open in cup shape, which flattens as tepals recurve by second day.

Tepalage: Typical of genus Lilium, with 6 imbricated tepals.

Tepal color: Flowers are distinguished by their soft red color pattern. The base of the tepals is R.H.S. C.C. Red 44 A, shading into a mix of R.H.S. C.C. Orange-Red 30 D and Red 40 B. The color is produced by anthocyanin pigments which are affected by light levels and temperature, therefore the red will intensify under cool temperatures and high light intensities. High light levels associated with high temperatures will degrade the pigment and cause the flowers a much softer red. Very low levels inhibit anthocyanin formation and cause a lighter flower color.

Tepal spotting: None.

Tepal longevity: Tepals stay on stems about two till three weeks.

Pedicel length: Most of the pedicels are 3 to 5 cm long, but a few may reach 6 cm.

Pedicel color: Dark green with plum overlay.

Pedicel form: Sturdy and ascending, up to 45 degrees from the horizontal.

Color changes: Flower color may change because of changes in temperature and lighting as the flower ages, as described under flower color.

Appearance: Flower is shiny.

Disease resistance: The plant is resistant to disease; in particular to Botrytis blight.

Fragrance: None.

Lasting quality: The flower is long lasting, both on the plant in a pot or on the plant in the garden.

THE REPRODUCTIVE ORGANS

Stamens: Arrangement typical of genus Lilium. Six stamens with soft green to palest pink filaments 7 to 9 cm long.

Pollen and anthers (dehisced): Close to R.H.S. C.C. greyed red 178A.

Pistil: One in number, 5 to 7 cm long.

Stigma: R.H.S. C.C. Red Group 44 B, small in size.

Characteristics of ovary: Characteristic of genus Lilium.

THE FRUIT

Fertility: The fruit is fertile.

Shape: Ovoid.

Color at maturity: Soft brown, sometimes overlaid with soft plum.

I claim:

1. A new and distinctive variety of Asiatic hybrid lily plant substantially as herein shown and described, characterized by its high resistance to disease; its vigorous growth and rapid natural propagation; and in particular by its unusual consistency close to its stem "outward-facing" red flowers are unique among Asiatic hybrid lilies.

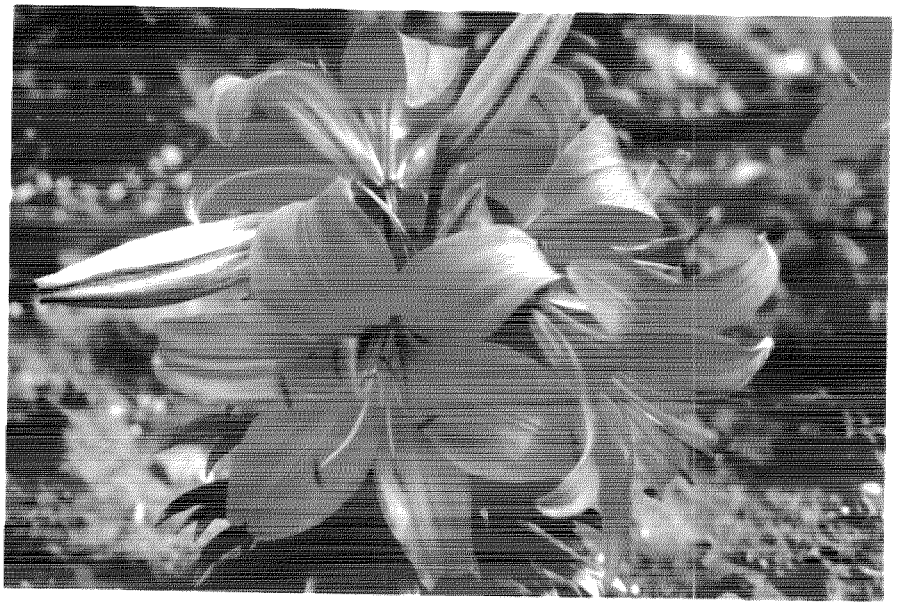

* * * * *